US00PP15134P2

(12) United States Plant Patent
Fischer

(10) Patent No.: US PP15,134 P2
(45) Date of Patent: Sep. 7, 2004

(54) APPLE TREE NAMED 'REBELLA'

(50) Latin Name: *Malus domestica*
Varietal Denomination: Rebella

(75) Inventor: Christa Fischer, Dresden (DE)

(73) Assignee: Bundesanstalt fur Zuchtungsforschung an Kulturpflanzen, Quedlinburg (DE)

( * ) Notice: Subject to any disclaimer, the term of this patent is extended or adjusted under 35 U.S.C. 154(b) by 0 days.

(21) Appl. No.: 10/371,813

(22) Filed: Feb. 21, 2003

(51) Int. Cl.[7] ..... A10H 5/00
(52) U.S. Cl. ..... Plt./161
(58) Field of Search ..... Plt./161

(56) References Cited

FOREIGN PATENT DOCUMENTS

HU P0001590 * 1/2002

OTHER PUBLICATIONS

UPOV–ROM GTITM Computer Database, 2003/04, GTI Jouve Retrieval Software, citation for 'Rebella'.*
http://www.bafz.de/baz99_e/baz_orte/dp/obst/apfel_rebella.htm.*

* cited by examiner

*Primary Examiner*—Anne Marie Grunberg
*Assistant Examiner*—S B McCormick-Ewoldt
(74) *Attorney, Agent, or Firm*—Webb Ziesenheim Logsdon Orkin & Hanson, P.C.

(57) ABSTRACT

A new and distinct *Malus domestica* plant that produces apples having a pleasant aroma and sweet taste suitable for use as a table fruit.

6 Drawing Sheets

Botanical classification: *Malus domestica.*
Varietal denomination: 'Rebella'.

BACKGROUND OF THE INVENTION

The present invention comprises a new and distinct cultivar of apple tree botanically classified as *Malus domestica* and known by the varietal name 'Rebella'. The new variety was discovered in 1986 in Dresden-Pillnitz. The new variety is the result of a planned breeding program between unpatented female parent 'Golden Delicious' and unpatented male parent 'Remo' ('James Grieve'×resistant clone). The purpose of the breeding program was to find a new cultivar with high disease resistance, high yield, and excellent fruit quality. The new variety exhibits similar disease resistance to 'Remo', but exhibits a different growing habit, taste, color, and ripening time than 'Remo'. The new variety exhibits a similar growing habit to 'Golden Delicious', but exhibits different disease resistance, taste, color, and ripening time than 'Golden Delicious'. Table 1 illustrates the differences between 'Rebella' and 'Golden Delicious'.

| | 'Rebella' | 'Golden Delicious' |
|---|---|---|
| Fruit Color | Red to reddish-yellow | Yellow |
| Taste | Sweet/acidic | Sweet |
| Ripening Time | September | October |
| Eating Time | September–November | October–April |
| Resistance | Resistant to scab, mildew, fire blight, and bacterial canker | None known to breeder |

The following characteristics distinguish the new variety from other *Malus domestica* varieties:

Fire blight resistance

Mildew resistance

Fruit firmness

Fruit shape

Fruit coloration

Taste

The new variety has been trial and field tested and has been found to retain its distinctive characteristics and remain true to type through successive propagations.

DESCRIPTION OF THE DRAWINGS

The accompanying photographic drawings illustrate the new cultivar, with the color being as nearly true as is possible with color illustrations of this type.

DESCRIPTION OF THE PLANT

Figure 1:
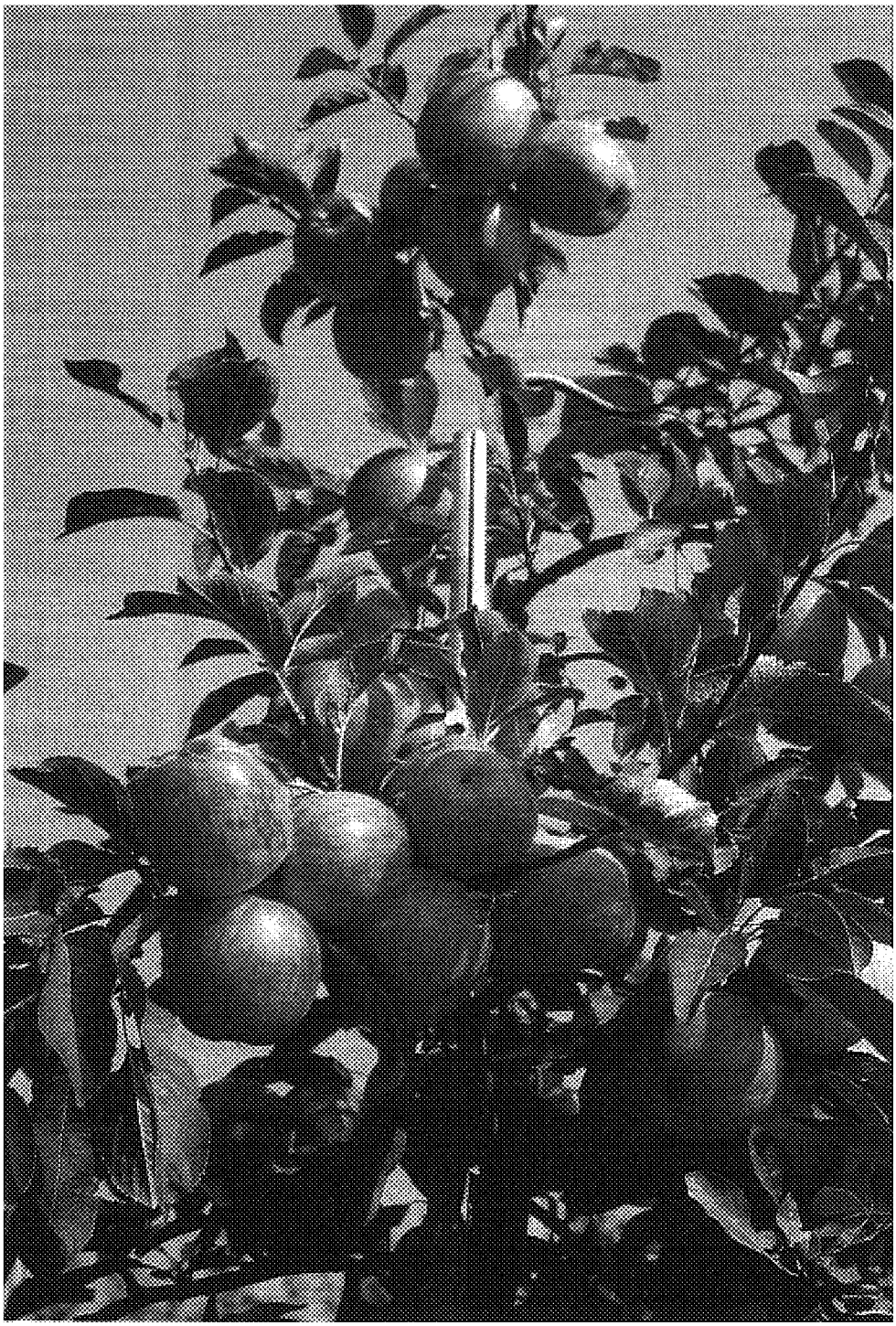
FIG. 1 shows the fruits of the new variety at maturity.
Figure 2:
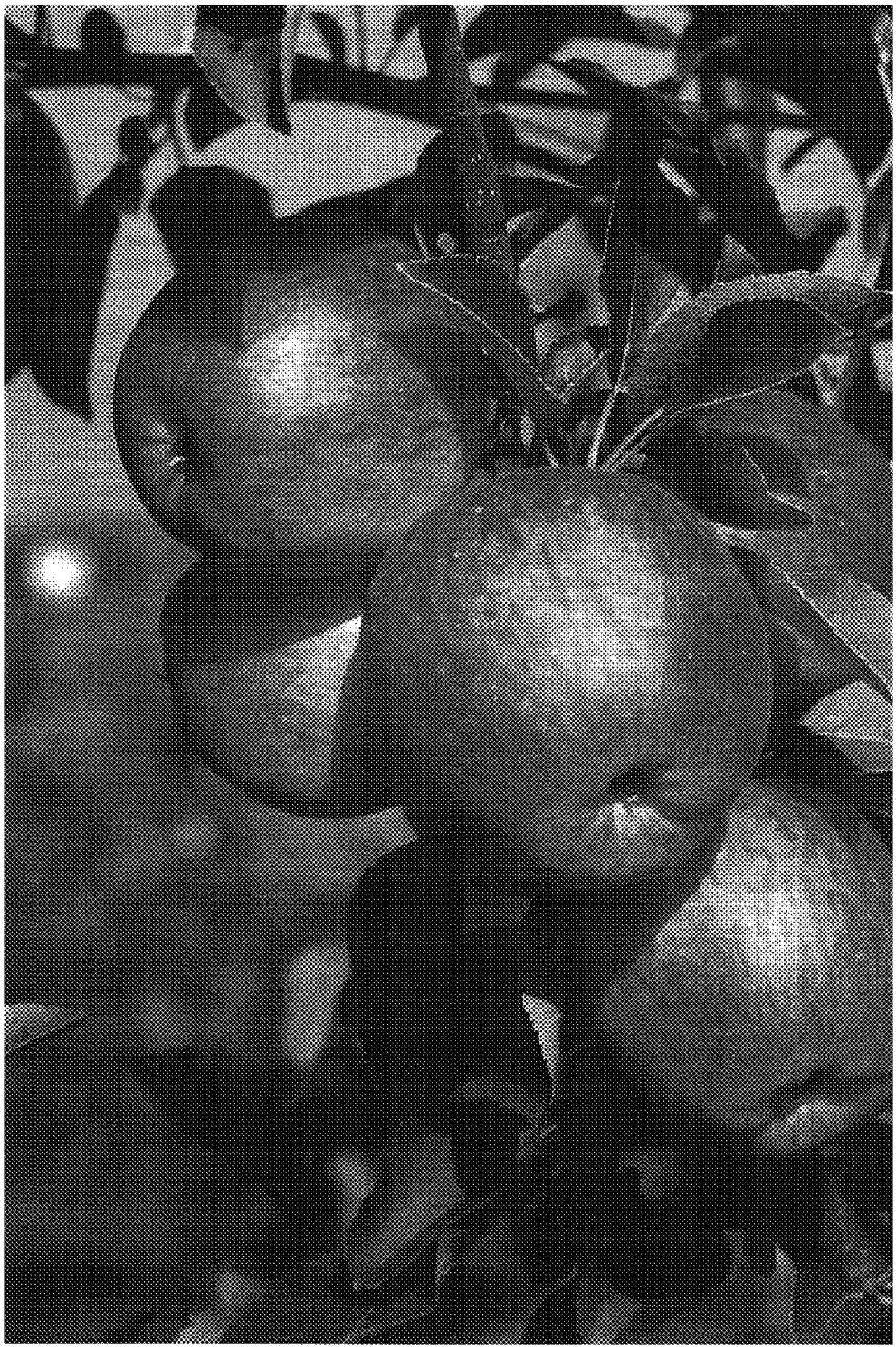
FIG. 2 shows a close-up view of the fruits of the new variety at maturity.
Figure 3:
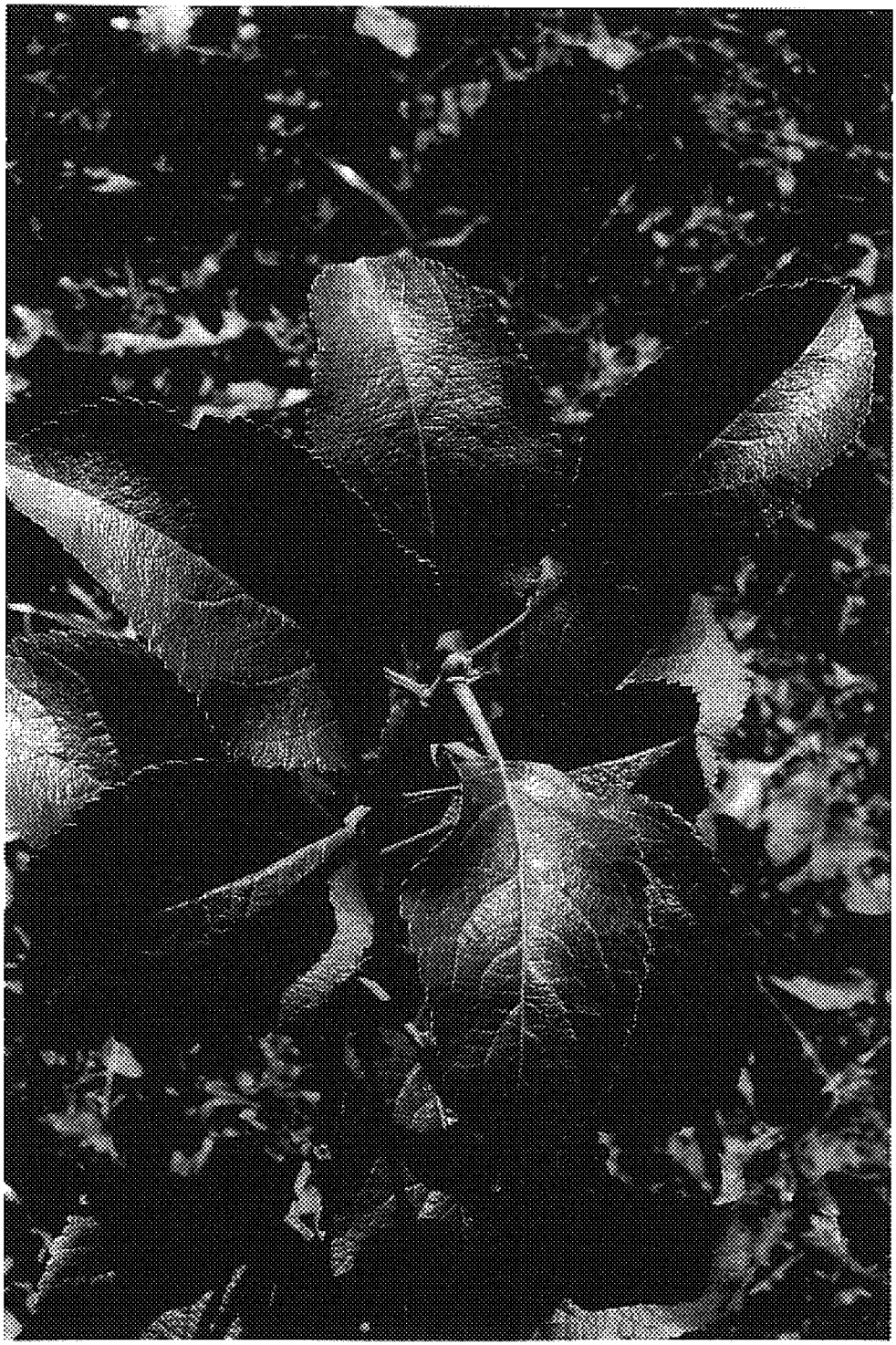
FIG. 3 shows the leaves of the new variety.
Figure 4:
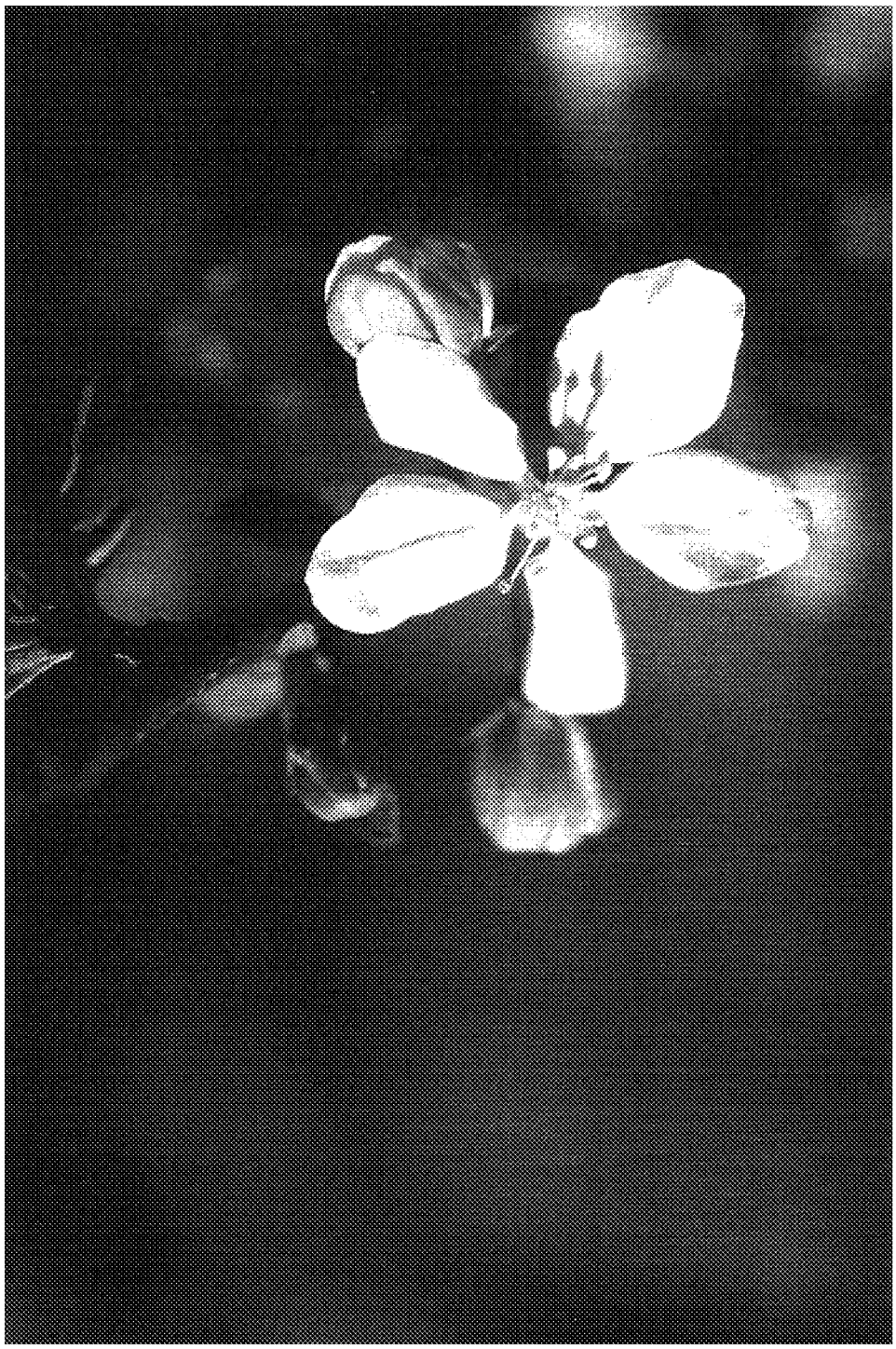
FIG. 4 shows an open blossom of the new variety.
Figure 5:
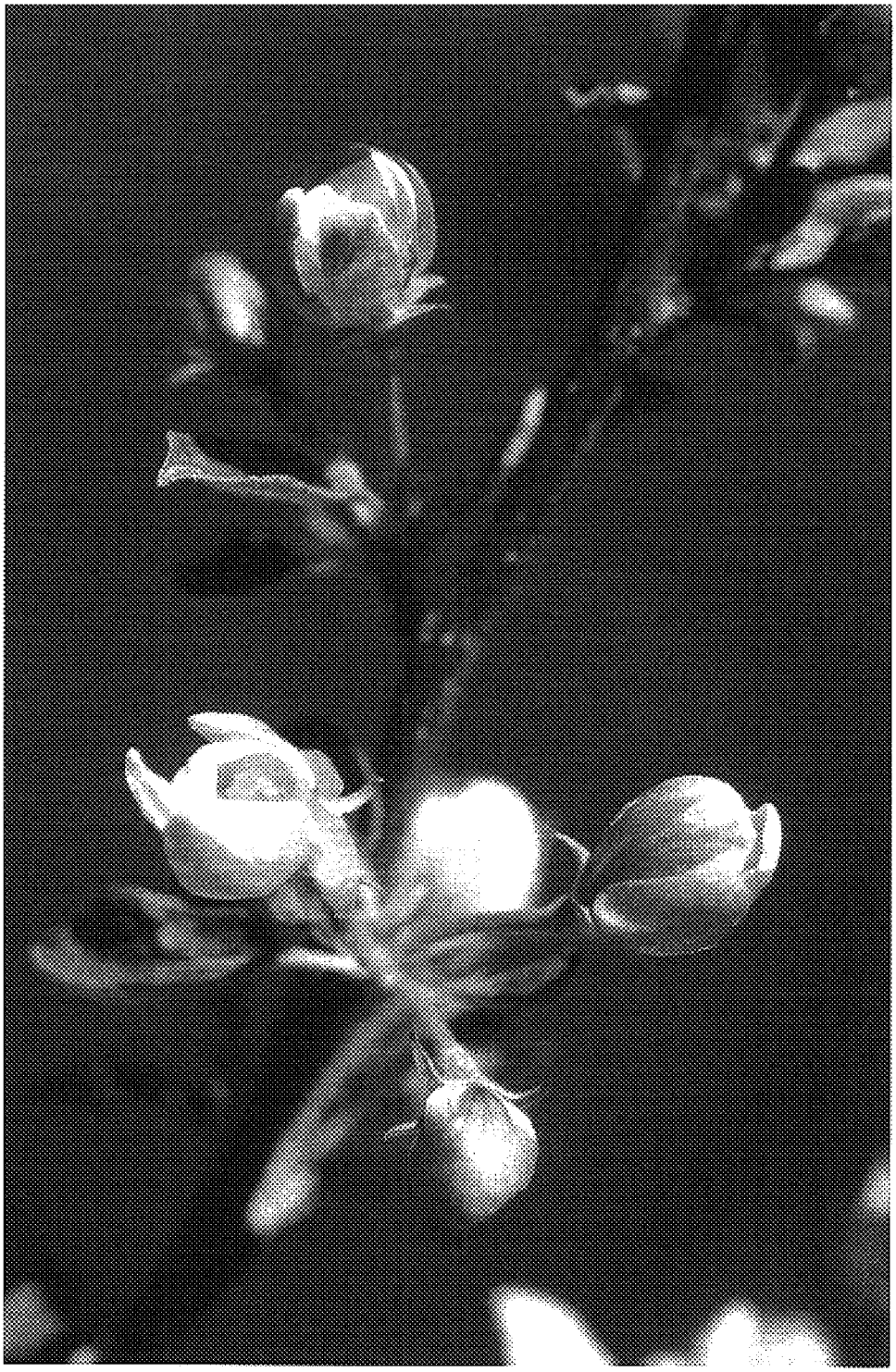
FIG. 5 shows the flower buds of the new variety.
Figure 6:
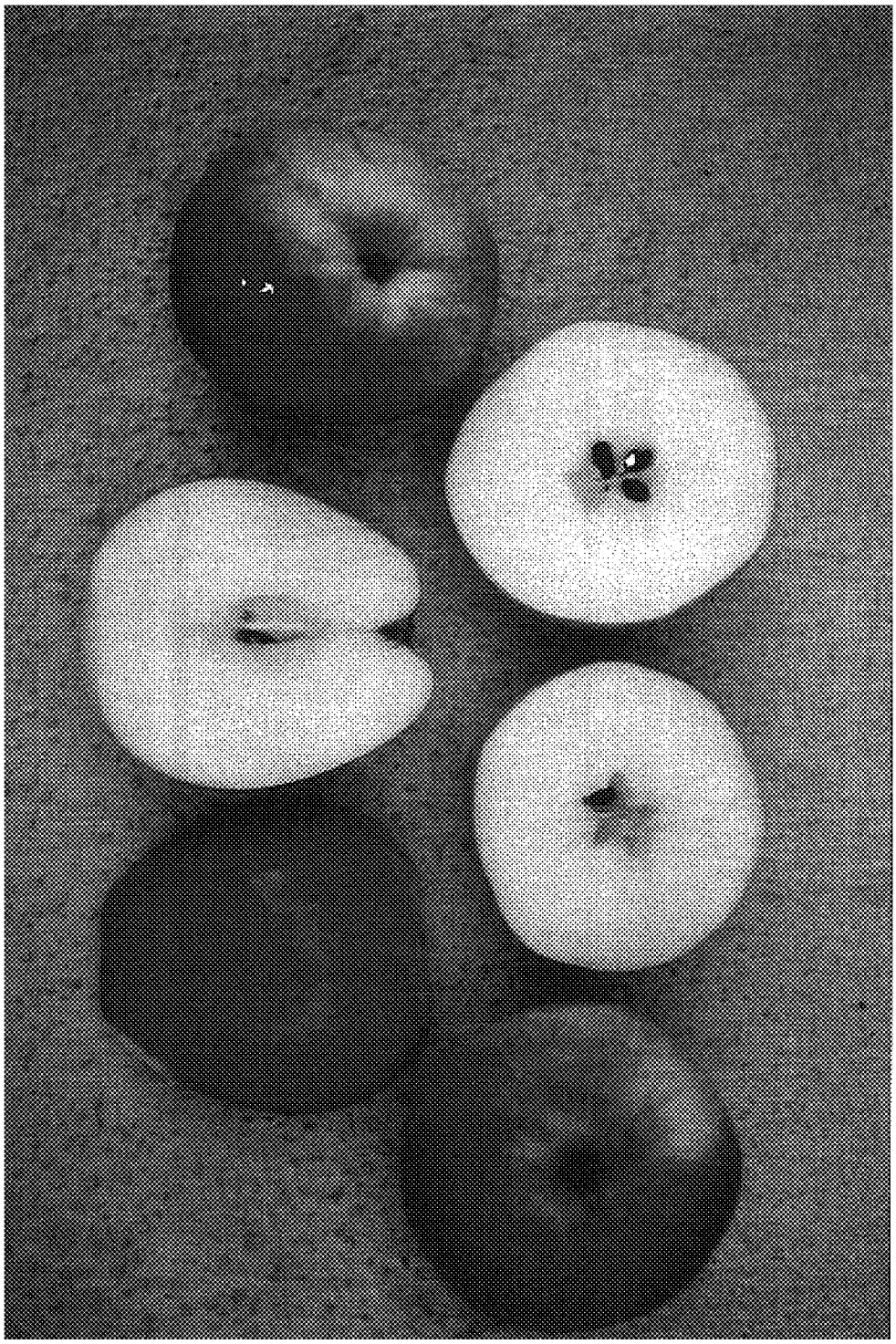
FIG. 6 shows cross section of the fruits of the new variety at maturity.

The following detailed description sets forth the characteristics of the new cultivar. The data which defines these characteristics were collected by asexual reproductions by grafting and budding first carried out in Dresden-Pillnitz in 1995. The new variety was grown in a 1.0 m by 3.5 m planting system field with typical fertilizer and no irrigation. The new variety was propagated and grown on M9 rootstock. The color readings were taken in natural daylight. Color references are primarily to The R.H.S. Colour Chart of The Royal Horticultural Society of London.

TREE

Age: 6 years.
Size: 2.8 m high; 2.0 m wide.

Density: Loose to medium.
Form: Spreading, upright, pyramidal.
Production: Very high.
Growth type: Similar to 'Golden Delicious'.
Trunk:
*Size.*—5 cm in diameter and 50 cm high at 4 years; 6.5 cm in diameter at 6 years on M9 rootstock.
*Surface texture.*—Smooth.
*Bark color.*—166A.
*Lenticels.*—Length: Average 6.0 mm (from 4–7 mm). Width: 2.0–3.0 mm. Color: Between 195C and 195D. Density: 32 per 10 $cm^2$.
Branches:
*Diameter.*—Main branches on the trunk 2–4 cm; at 1 year 8–10 mm.
*Surface texture.*—Smooth.
*Color.*— 1 year: Between 166A and 166B. 2–3 years: 200C.
*Form.*—Rounded.
*Average angle.*—70–80°.
*Bud arrangement.*—Alternate. Internode: 3–4 cm.
*Lenticels.*—Length: 4.0 mm. Width: 0.2–0.4 mm. Shape: Oval to round. Density: 21 per 10 cm of branch length. Color: 161C.
Leaves:
*Length.*—Average of 87 mm at 1 year.
*Width.*—Average of 61.4 mm at 1 year.
*Form.*—Ellipsoidial; egg-shaped.
*Base.*—Symmetric.
*Apex.*—Abruptly acute.
*Margin.*—Crenulate.
*Pubescence.*—Upper surface: Very weak; smooth. Lower surface: Weak.
*Color.*—Young leaves: Upper surface: 143A. Mature leaves: Upper surface: 137. Lower surface: 139A.
*Petiole.*—Length: Average 25.2 mm. Diameter: 2 mm. Color: Between 141B and 143A.
*Veins.*—Venation type: Well proportioned; net-like. Color: Upper surface: 148D. Lower surface: Between 148A and 148B.
Flowers:
*Blooming time.*—Middle to late; 2 days before 'Golden Delicious'.
*Blooming period.*—12–15 days.
*Pollination requirements.*—Diploid; self-sterile; needs pollinator.
*Number of flowers per cluster.*—5 to 7.
*Fragrance.*—Mild.
*Buds* (*terminal buds described in winter*).—Length: 9 mm. Width: 4–5 mm. Color: 200B.
*Petals.*—Number: 5. Length: Average 22 mm. Width: 9–10 mm. Shape: Oblong. Aspect: Color: 62D when fully open. Margin: Entire. Appearance: Solitary; rotate; petals unfused.
*Color.*—When opening: Upper surface: Between 64C and 64D. Lower surface: 64C. When fully opened: Upper surface: 62D. Lower surface: Between 62C and 62D.
*Sepals.*—Shape: Tapering; rough. Margin: Entire. Texture: Rough. Length: 3–4 mm. Width: 1–1.5 mm. Color: Upper surface: 138A. Lower surface: 139B.
*Stamens.*—Number (per flower): 12–15. Filament length: 4–6 mm.
*Anthers.*—Shape: Oblong. Length: 2 mm. Diameter: 0.8 mm. Color: 4.
*Pollen.*—Color: 7. Amount (generally): Heavy.
*Pistils.*—Length: 0.8 cm; variable.
*Style.*—Length: 5 mm. Color: Between 154B and 154C.
*Stigma.*—Shape: Rounded. Color: 154D; with alterations at flowering time.
Fruit:
*Maturity when described.*—Fully ripened.
*Date of picking.*—Between September 15 and September 20.
*Size.*—Axial diameter: Average 67 mm (from 65–70 mm). Transverse diameter: Average 65 mm (from 63–68 mm).
*Form.*—Oblong; ellipsoidal-conical.
*Weight.*—Average of 10 fruits weighed was 131 g.
*Cavity.*—Depth: 1–1.5 cm. Width: 1.8–2.2 cm.
*Basin.*—Depth: 0.8–1.2 cm. Width: 1.6–2.0 cm.
*Calyx.*—Small; typical.
Skin:
*Thickness.*—Thin; firm.
*Texture.*—Smooth.
*Tendency to crack.*—No cracking.
*Color.*—Generally 45B; varies between 45A–45C.
*Ground color.*—4B.
Flesh:
*Aroma.*—Tasty; strong.
*Color.*—8D.
*Texture.*—Crisp; firm.
*Eating quality.*—Very good; sweet with well-balanced acid.
Core:
*Calyx tube.*—Closed.
*Styles.*—If present, 0.1 mm.
Stamens:
*Axillary cavity.*—Middle deep.
*Seed cells.*—Wall: Firm, hardy. Depth: 11–12 mm from the middle axis. Breadth: 4 mm.
*Longitudinal section.*—Ovate.
Seeds:
*Number perfect.*—8.
*Number in one cell.*—1–2.
*Locules.*—Average number: 5. Average length: 10.4 mm. Average width: 5.7 mm.
*Length.*—10–11 mm.
*Width.*—5.0–5.5 mm.
*Form.*—Oblong.
*Color.*—Between 166A and 166B.
Stem:
*Length.*—1–1.5 cm.
*Width.*—1.8–2.2 mm.
*Color.*—Between 137A and 137B with some fruits between 164A and 165B.
Use: Table fruit.
Shipping quality: Good for one month after picking.
Keeping quality: Two months.
Tree winter hardiness: Hardy.
Bud winter hardiness: Hardy.
Drought tolerance: Not tested.
Disease resistance: Fire blight; mildew; scab; red spider mite; pseudomonas; partial to aphids.

I claim:

1. A new and distinct variety of *Malus domestica* plant substantially as shown and described.

* * * * *

UNITED STATES PATENT AND TRADEMARK OFFICE

CERTIFICATE OF CORRECTION

PATENT NO. : PP 15,134 P2
DATED : September 7, 2004
INVENTOR(S) : Christa Fischer It is certified that error appears in the above-identified patent and that said Letters Patent is hereby corrected as shown below:

Column 1,
Before the table, insert -- Table 1 --.

Column 4,
Lines 42-43, delete "*Locules,* —Average number: 5. Average length: 10.4 mm. Average width: 5.7 mm.".
Line 47, after "*Color*" insert -- *Locules,* —Average number: 5. Average length: 10.4 mm. Average width: 5.7 mm. --.

Signed and Sealed this

Eighteenth Day of April, 2006

JON W. DUDAS
*Director of the United States Patent and Trademark Office*